United States Patent [19]

Stookey

[11] 4,083,252

[45] Apr. 11, 1978

[54] FLOW PROPORTIONAL LIQUID SAMPLER

[76] Inventor: Lawrence Lynn Stookey, 105½ N. Franklin, Manchester, Iowa 52057

[21] Appl. No.: 818,880

[22] Filed: Jul. 25, 1977

[51] Int. Cl.² ............................................. G01N 1/24
[52] U.S. Cl. ................................................ 73/421 B
[58] Field of Search ...................................... 73/421 B

[56] References Cited

U.S. PATENT DOCUMENTS

| | | | |
|---|---|---|---|
| 3,478,596 | 11/1969 | Farrell, Jr. | 73/421 B |
| 3,587,670 | 6/1971 | Brailsford | 73/421 B |
| 3,924,471 | 12/1975 | Singer | 73/421 B |
| 3,949,611 | 4/1976 | Watt | 73/421 B |

Primary Examiner—S. Clement Swisher

Attorney, Agent, or Firm—Wm. T. Metz

[57] ABSTRACT

A means to obtain a sample of raw sewage entering a sewage treatment and disposal plant so that the sample is taken during a fixed portion of the time that raw sewage flows into the treatment area of the sewage treatment and disposal plant and is of a constant volume comprised of a vacuum pump with a percentage timer to draw raw sewage through a stand pipe into a sample vessel so that the raw sewage will rise above the top of the stand pipe and then, due to the action of an imperfect flap valve, fall to the level of the top of the stand pipe and remain at this level until the percentage timer deactivates a solenoid valve causing atmospheric pressure to allow a constant volume sample to flow into a sample container.

3 Claims, 1 Drawing Figure

FLOW PROPORTIONAL LIQUID SAMPLER

BACKGROUND OF THE INVENTION

1. Field of the Invention

This invention pertains to a liquid sampler which will obtain a constant volume time-proportional sample from a sewage treatment and disposal plant as the raw sewage is processed in the treatment and disposal plant, such as are commonly in use in the cities and towns throughout the United States and other places in the world, to sample the raw sewage being taken into the treatment and disposal plant in order to obtain a bacteria count, percentage of solids and other data necessary to be known in order to determine the amount of chemicals and treatment to be given the raw sewage taken into the sewage treatment and disposal plant. Since the maximum output of a given sewage treatment and disposal plant is a function of time this information is critical.

BACKGROUND OF THe INVENTION

2. Description of the Prior Art

Heretofore samples taken of raw sewage as it enters a sewage treatment and disposal plant have been done in a number of ways. The most basic, of course, is by hand with a dip bucket. The liquid level of the raw sewage in a sewage line or a wet well holding area before entering the treatment area of the sewage treatment and disposal plant may vary a great deal, depending upon sewage flow at any given time. It is, thus, highly desirable to be able to obtain samples of the raw sewage for processing no matter what the liquid level of the raw sewage in the sewage line or wet well holding area. There exist devices to take constant volume samples, but they may not be time proportional. Other devices allow flow proportional sampling, but usually with associated flow measurement equipment. The present invention uses no auxiliary flow measuring equipment, and a vacuum system, rather than pressure of peristaltic pumping, to move the sample.

SUMMARY OF THE INVENTION

This invention provides a means to obtain constant volume time-proportional samples of raw sewage from a sewage line or a wet well holding area as said raw sewage is flowing into the treatment areas of a sewage treatment and disposal plant.

It is, therefore, an object of this invention to provide a sampling device to obtain constant volume time-proportional samples of raw sewage in sewage treatment and disposal plants.

It is a further object of this invention to provide a sampling device to obtain constant volume time-proportional samples in a sewage treatment and disposal plant which will work automatically and without constant supervision.

It is a further object of this invention to provide a means to obtain constant volume time-proportional samples from the raw sewage lines or holding wells of a sewage treatment and disposal plant which will not vary in volume due to the change in the liquid level of the raw sewage in the lines or the wet well holding area.

Further objects and advantages of this invention will become apparent from the following drawing, description and claims.

DESCRIPTION OF THE PREFERRED EMBODIMENT

Figure 1:
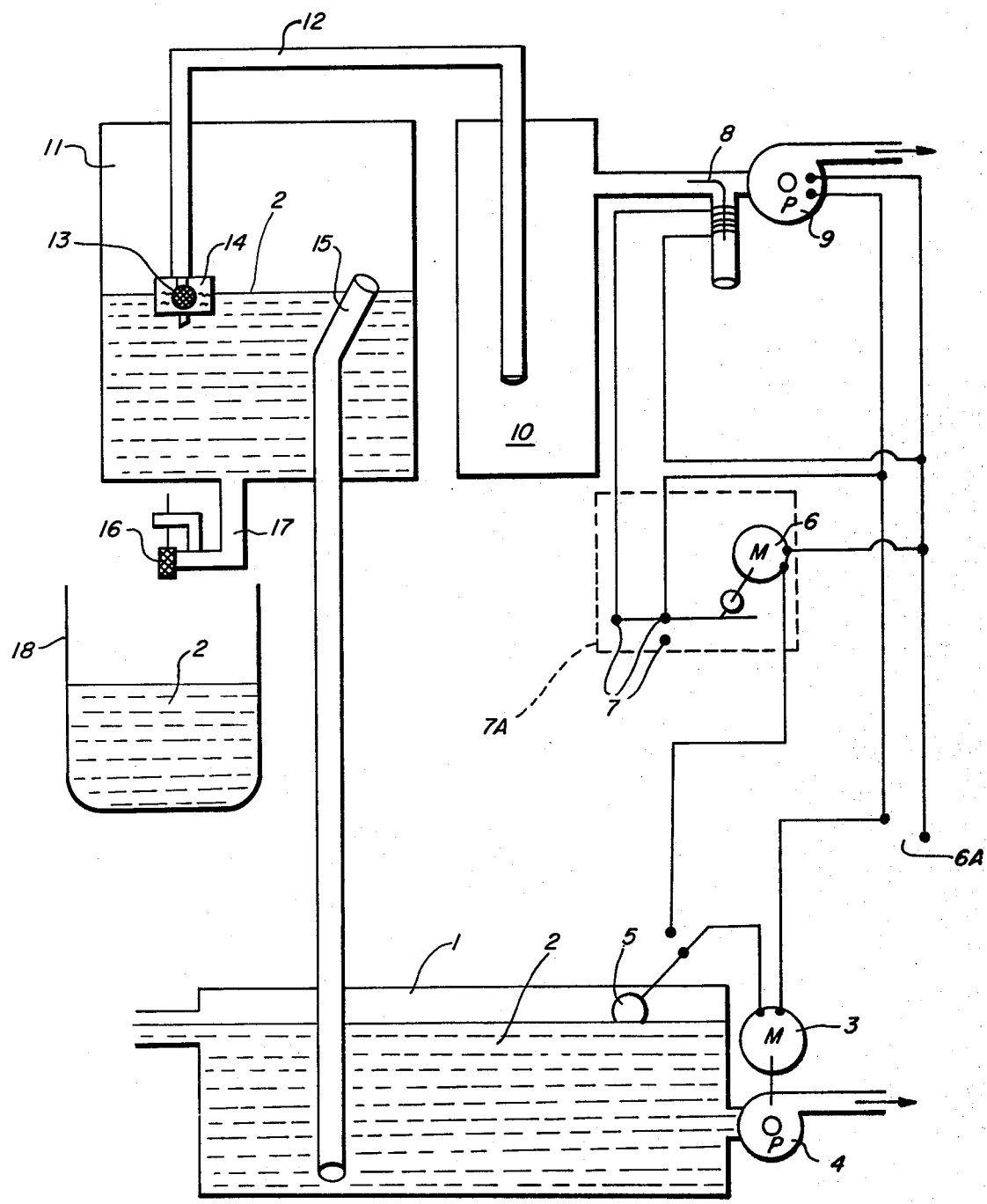
FIG. 1 is a diagramatic representation of the constant volume time-proportional liquid sampler showing a connection to a wet well of a sewage treatment and disposal plant.

Referring now to the drawing, a wet well 1 contains raw sewage 2. A pump motor 3 is connected to a centrifugal pump 4. A liquid level float switch 5 is connected in series with a drive motor 6 across a source of electrical energy 6A. Switch contacts 7 of a percentage timer 7A are connected in series with solenoid valve 8. A vacuum pump 9 is connected through a trap 10 to sample vessel 11 by means of an inverted U-shaped pipe 12. A ball valve 13 is contained in a valve seat box 14 at the end of pipe 12 located in vessel 11. A stand pipe 15 runs from sample vessel 11 into the wet well 1 and extends below the lower limit of the liquid level of the raw sewage 2. A flap valve 16 is connected at the lower end of a pipe 17 extending from the sample vessel 11 to a sample container 18.

DESCRIPTION OF OPERATION

When the level of the raw sewage 2 in the wet well 1 rises to a point where liquid level float switch 5 closes, the pump motor 3 starts and causes the centrifugal pump 4 to pump the raw sewage 2 into the treatment area (unshown) of a sewage treatment and disposal plant. When this situation occurs it is desirable to obtain a sample of the raw sewage being pumped into said treatment area. Prior to the drive motor 6 being activated, solenoid valve 8 is in such a position that the vacuum pump 9, which is constantly running, does not evacuate the system composed of the trap 10 and the sample vessel 11, but rather the system is open to atmospheric pressure. However, upon the float switch 5 being closed the drive motor 6 is activated, opening the contacts 7 and causing the solenoid valve 8 to connect the vacuum pump 9 to the trap 10. When this process is started there is no liquid in the sample vessel 11 in that all of it has been drained from the previous cycle of operation. As the vacuum builds up in the trap 10 and the sample vessel 11 connected by the inverted U-shaped pipe 12, raw sewage is drawn through the stand pipe 15 into the sample vessel 11. Flap valve 16 is sealed shut due to the vacuum created by the vacuum pump 9 and ball valve 13 closes when the liquid level of raw sewage 2 passes the lower end of the inverted U-shaped pipe 12 in sample vessel 11. When the ball valve 13 closes, the source of vacuum from the vacuum pump 9 is cut off, however the liquid level of the raw sewage 2 continues to rise above the level of the top of the stand pipe 15 and the valve seat box 14 until the vacuum in the space above the liquid level in the sample vessel 11 comes close to pressure equilibrium with the suction head. That is to say that at this point in time of the cycle the vacuum in the space above the liquid level in sample vessel 11 has fallen to a point where it is equal to the number of feet of liquid above the level of the raw sewage 2 in the wet well 1.

The flap valve 16 is designed so as to have an imperfect seal on the outlet pipe 17 and when the liquid level in the sample vessel 11 reaches the pressure equilibrium with the suction head the flap valve 16 will begin to leak air rather rapidly into the vessel 11, causing the liquid level to descend to just above the top of the stand pipe 15 where it will remain until the drive motor 6 of the percentage timer 7A has once again closed the switch contacts 7, causing the solenoid valve 8 to open the system to atmospheric pressure. As the liquid level is descending to the top of the stand pipe 15 the excess liquid returns through the stand pipe 15 to the wet well 1, purging and cleaning the stand pipe 15. As atmospheric pressure returns to the system the weight of the liquid in the sample vessel 11 causes the flap valve 16 to open, allowing the sample of raw sewage 2 now contained in the sample vessel 11 to flow by gravity through the pipe 17 into the sample container 18. It can thus be seen that a constant volume sample of raw sewage 2 is obtained in each cycle. The process is repeated at constant intervals of time when the centrifugal pump 4 is in operation as soon as the liquid level float switch 5 is closed and the drive motor 6 of the percentage timer 7A is in operation, giving a constant volume time-proportional sample. Various sample containers 18 may be used and thus a number of samples may be so collected and stored in temperature controlled storage areas until analysis of the samples can be completed.

The percentage timer 7A will open the contacts 7 for a period to be predetermined which is a percentage of the period of time that the motor 3 is driving the pump 4 pumping raw sewage 2 into the treatment area of the sewage treatment and disposal plant. This invention makes it possible to obtain a sample for a given percentage of time during the operation of the pump 5. A 10% sample has been used in practice. That is, for every fifteen minutes the pump 4 is operating the entire sampling cycle takes a period of 1.5 minutes during which one constant volume sample is obtained. The sample is, therefore, proportional to the flow of raw sewage 2 into the treatment area of the sewage treatment and disposal plant.

I claim:
1. A flow proportional liquid sampler comprised of
 (a) a vacuum pump connected to a trap through a solenoid valve,
 (b) an inverted U-shaped pipe connecting the trap to a sample vessel and extending vertically into the top of the trap and the sample vessel,
 (c) the solenoid valve having an opening to the atmosphere,
 (d) a valve seat box containing a ball valve connected on the end of the inverted U-shaped pipe in the sample vessel,
 (e) a stand pipe in the sample vessel running to a source of liquid to be sampled,
 (f) the upper end of the stand pipe being at the same elevation as the ball valve,
 (g) an outlet pipe attached to the lower portion of the sample vessel and positioned over a sample container,
 (h) a flap valve having an imperfect seal attached to the end of the outlet pipe positioned over the sample container,
 (i) a percentage timer to control the solenoid valve so as to first create a vacuum in the sample vessel and then open the sample vessel to atmospheric conditions.

2. The flow proportional liquid sample of claim 1 wherein the percentage timer activates the solenoid valve to create a vacuum in the sample vessel during a fixed percentage of the time that liquid is running through the area to be sampled.

3. The flow proportional sampler of claim 2 wherein the imperfect seal of the flap valve allows air to leak into the sample vessel when the liquid to be sampled attains an elevation above the top of the stand pipe and the ball valve.

* * * * *